(12) United States Patent
Nishimura et al.

(10) Patent No.: US 7,803,533 B2
(45) Date of Patent: Sep. 28, 2010

(54) DIAGNOSTIC AGENT FOR MALIGNANT MELANOMA

(75) Inventors: Yasuharu Nishimura, Kumamoto (JP); Tetsuya Nakatsura, Kumamoto (JP)

(73) Assignee: Kumamoto Technology & Industry Foundation, Kumamoto (JP)

( * ) Notice: Subject to any disclaimer, the term of this patent is extended or adjusted under 35 U.S.C. 154(b) by 537 days.

(21) Appl. No.: 10/577,343

(22) PCT Filed: Oct. 28, 2004

(86) PCT No.: PCT/JP2004/016374

§ 371 (c)(1),
(2), (4) Date: Mar. 5, 2007

(87) PCT Pub. No.: WO2005/039380

PCT Pub. Date: May 6, 2005

(65) Prior Publication Data

US 2008/0044818 A1  Feb. 21, 2008

(30) Foreign Application Priority Data

Oct. 29, 2003  (JP) .............................. 2003-368725

(51) Int. Cl.
*C12Q 1/68* (2006.01)
(52) U.S. Cl. ........................................................ 435/6
(58) Field of Classification Search ............... 435/6
See application file for complete search history.

(56) References Cited

U.S. PATENT DOCUMENTS

| 5,730,981 A | 3/1998 | Bosslet et al. | |
|---|---|---|---|
| 5,874,560 A | 2/1999 | Kawakami et al. | |
| 2003/0165954 A1* | 9/2003 | Katagiri et al. | 435/6 |
| 2006/0251666 A1 | 11/2006 | Nakatsura et al. | |

FOREIGN PATENT DOCUMENTS

JP  6-46882  2/1994
JP  10-505481  6/1998

OTHER PUBLICATIONS

Desai et al. (J. Med. Genet. 35:476-481 (1998)).*
Smith et al. (Vet. Pathol. 39:651-678 (2002)).*
Rutler et al. (Sem. Oncol. 29(4):370-381 (2002)).*
Bergkvist et al. (Genet. Engineer. News 28(13):26 and 28 (Jul. 2008)).*
Bustin et al. (Gen. Eng. News 29(14):40-42 (Aug. 1, 2009).*
Liang et al. (Funct. Integr. Genomics 6:1-13 (2006)).*
Preston (Environ. Molec. Mutagenesis 45:214-221 (2005)).*
Meyer et al. (Clin. Rev. Biochem. & Molec. Biol. 39:197-216 (2004)).*
Busesa et al. (J. Neuropathol. Exp. Neurol. 63(10):1003-1014 (2004); Abstract).*
Kim et al. (J. Invest. Derm. 92(2):210-216 (1989) Abstract.*
Nakatsura et al. (Clin. Can. Res. 10:6612-6621, (Oct. 4, 2004).*
Tetsuya Nakata et al., "Glypican-3, overexpressed specifically in human hepatocellular carcinoma, is a novel tumor marker", Biochemical and Biophysical Research Communications, 306, (2003), pp. 16-25.
Saikali et al., "Expression of glypican 3(GPC3) in embryonal tumors," International Journal of Cancer, vol. 89, No. 5, pp. 418-422 (2000).
Cappuro et al., "Overexpression of glypican-3 human hepatocellular carcinomas determined by i mmunohistochemistry using a monoclonal antibody," Proceedings of the Annual Meeting of the American Association for Cancer Research, vol. 43, p. 219 (2002).
English language abstract of EP0561183 (corresponding to JP 6-46882 A, published Feb. 22, 1994), provided by esp@cenet.
English language abstract of WO 95/29193 (corresponding to JP 10-505481, published Jun. 2, 1998) and provided by esp@cenet.
U.S. Appl. No. 12/063,165 (Nishimura et al.) filed Feb. 7, 2008, and entitled "Glypican-3 (GPC-3)-Derived Tumor Rejection Antigenic Peptides Useful for HLA-A2-Positive Patients and Pharmaceutical Comprising the Same."
U.S. Appl. No 12/155,864 (Nakatsura et al.) filed Jun. 11, 2008, and entitled "Cancer Antigen and Use Thereof."
U.S. Appl. No. 11/577,435 (Nishimura et al.), filed Apr. 18, 2007, and entitled "Novel Diagnostic Kit for Malignant Melanoma."

* cited by examiner

*Primary Examiner*—Lynn Bristol
(74) *Attorney, Agent, or Firm*—Greenblum & Bernstein, P.L.C.

(57) ABSTRACT

An object of the present invention is to provide a novel and clinically useful diagnostic agent for malignant melanoma. The present invention provides a diagnostic agent for malignant melanoma, which comprises an antibody against GPC3, or a probe or a primer capable of detecting GPC3 expression.

4 Claims, 4 Drawing Sheets

DIAGNOSTIC AGENT FOR MALIGNANT MELANOMA

TECHNICAL FIELD

The present invention relates to a diagnostic agent and a diagnostic kit for malignant melanoma and a diagnostic method for malignant melanoma.

BACKGROUND ART

Melanoma is one type of skin cancer referred to as malignant melanoma. There are various types of skin cancer. Melanoma is the type of skin cancer that has the highest grade of malignancy. Among cells composing skin, melanin-pigment-producing cells are referred to as pigment-producing cells (melanocytes). These cells become cancerous and melanoma is developed.

The frequency of the occurrence of melanoma in Japan is approximately 1.5 to 2 people per population of 100,000. It is inferred that melanoma annually occurs among approximately 1,500 to 2,000 people in Japan. In the Europe and the United States, the frequency of melanoma incidence is said to be over a dozen people per population of 100,000. The frequency of melanoma incidence in Australia is 20 or more people per population of 100,000, which is said to be the highest in the world. Accordingly, people in Europe, the United States and Australia are interested in melanoma and pay attention to its occurrence. Surprisingly, it has been confirmed that the frequency of the occurrence of melanoma is increasing yearly in both Japan and countries other than Japan. In the latest survey, the annual number of fatalities due to this disease in Japan was as high as around 450 people. Melanoma afflicts people regardless of age. Melanoma occurs more frequently particularly among people aged 40 and up and occurs most frequently occurs among people aged 60 to 70 and up. Melanoma occurs infrequently among children, but this does not mean that no melanoma occurs among children. Currently, melanoma tends to occur more frequently among young people aged 20 to 30 and up. There are no particular tendencies for melanoma to occur more frequently either in males or females. Melanoma occurs in both males and females. Melanomas in Japanese people are most frequently developed on the soles of the feet (planta pedis). Such melanoma cases account for approximately 30% of all melanoma cases in Japan. Melanomas in Japanese people are characterized in that they are often developed in the toenails and fingernails. Furthermore, similar to melanomas in Western people, melanomas in Japanese people are developed at all skin locations, such as in the trunk, hands, feet, face, head, and the like.

Serum tumor marker measurement is important not only in melanoma diagnosis, but also in early detection of recurrence in postoperative cases and in determination of therapeutic effects in cases at progressive stages. As tumor markers for melanoma, the usefulness of serum LDH and of 5-S-cysteinyldopa (5-S-CD) have been known to date. In more recent years, an S-100β protein and a melanoma inhibitory activity (MIA) have been reported as more sensitive markers. In Japan, 5-S-CD is broadly used as a tumor marker for melanoma. However, none of these tumor markers yield positive results unless the melanoma tested for is at a highly advanced stage, such as Stage IV. Therefore, it must be said that the usefulness of these tumor markers is limited in terms of melanoma diagnosis and early detection of postoperative recurrence.

The present inventors have previously examined the expression profiles of 23,040 types of genes in 20 types of primary hepatocellular carcinoma (HCC) and in various normal organs, including those in prenatal periods, with the use of a genome-wide cDNA microarray containing such genes. As a result, the present inventors have discovered that glypican-3 (GPC3) is highly expressed in most HCC types, whereas GPC3 is expressed in the liver, kidney, and lungs during the prenatal period and is hardly expressed in an adult's normal organs other than the placenta. Moreover, the present inventors have reported that the glypican-3 (GPC3) is a secretory protein, that GPC3 can be detected in the sera of 40% of HCC patients using the ELISA method, and that GPC3 is useful as a novel tumor marker for HCC (Nakatsura T. et al., Biochem. Biophys. Res. Commun. 306, 16-25 (2003)).

In 1996, Pilia et al. reported that glypican-3 (GPC3) encoding one member of glypican family is mutated in Simpson-Golabi-Behmel syndrome (SGBS) patients (Pilia G et al., Nat. Genet. 12, 241-247 (1996)). SGBS is an X-linked disorder characterized by pre- and postnatal overgrowth and wide-ranging clinical expression, ranging from a very mild phenotype in female carriers to lethal symptoms in male infants (Neri G et al., Am. J. Med. Genet. 79, 279-283 (1998)). Examples of clinical features of SGBS include distinct facial appearance, cleft palate, ankylodactylia, hyperdactylia, accessory nipples, cystic disease of kidney, renal dysplasia, and congenital heart disease (Behmel A et al., Hum. Genet. 67, 409-413 (1984); Garganta C. L. and Bodurtha J. N., Am. J. Med. Genet. 44, 129-135 (1992); Golabi M and Rosen, L., Am. J. Med. Genet. 17, 345-358 (1984); and Gurrieri F et al., Am. J. Med. Genet. 44, 136-137 (1992)). It has been reported that most GPC3 mutations are point mutations or deletions of several nucleotides including exons (Hughes-Benzie R. M. et al., Am. J. Med. Genet. 66, 227-234 (1996); Lindsay S. et al., J. Med. Genet. 34, 480-483 (1997); Veugelers. M. et al., Hum. Mol. Genet. 9, 1321-1328 (2000); and Xuan J. Y. et al., J. Med. Genet. 36, 57-58 (1999)). Moreover, because of the lack of correlation between a patient's phenotype and a mutation location, SGBS may be induced by the deletion of a functional GPC3 protein or by other genetic factors relating to the relevant phenotype within a family and between families (Hughes-Benzie R. M. et al., Am. J. Med. Genet. 66, 227-234 (1996)). A study on GPC3-deficient mice has also supported this hypothesis (Cano-Gauci D. F. et al., J. Cell Biol. 146, 255-264 (1999)). Such mice have some abnormalities that are observed in SGBS patients, such as overgrowth, cystic disease of kidney, and renal dysplasia.

It has been reported that based on studies using Northern blot analysis, GPC3 mRNA is overexpressed in HCC, placenta, fetal liver, fetal lungs, and fetal kidney (Zhu Z. W. et al., Gut 48, 558-564 (2001); Hsu. H. C. et al., Cancer Res. 57, 5179-5184 (1997); and Pellegrini M. et al., Dev Dyn. 213, 431-439 (1998)).

Moreover, it has been reported that since GPC3 is a cell proliferation inhibitor and can induce apoptosis in a type of tumor cells (Cano-Gauci D. F. et al., J. Cell Biol. 146, 255-264 (1999); and Duenas Gonzales A. et al., J. Cell Biol. 141, 1407-1414 (1998)), GPC3 expression is down-regulated in tumors derived from various origins. Lin et al. have demonstrated that GPC3 is expressed in the normal ovary, but cannot be detected in specific types of ovarian cancer cell lines (Lin H. et al., Cancer Res. 59, 807-810 (1999)). In all cases where no GPC3 expression was observed, the GPC3 promoter was hypermethylated, no mutations were found in the coding regions, and GPC3 expression was recovered through treatment with a demethylating agent. It has been further reported that the ectopic expression of GPC3 inhibits colony-forming activity in several types of ovarian cancer cell lines. Other data that relates GPC3 to cancer are data obtained by a differential mRNA display study concerning normal rat mesothelial cells and mesothelioma cell lines (Murthy S. S. et al., Oncogene 19, 410-416 (2000)). In this study, it was discovered that GPC3 is always downregulated in tumor cell lines. Furthermore, similar downregulation has also been observed in primary rat mesothelioma- or human mesothelioma-derived cell lines. Similar to the cases of ovarian cancer, no mutations have been discovered in the GPC3-encoding sequence; however, abnormal methylation in the GPC3 promoter region has been observed in most cell lines. As reported (Duenas Gonzales A. et al., J. Cell Biol. 141, 1407-1414 (1998)), it has been demonstrated that the ectopic expression of GPC3 in mesothelioma cell lines inhibits colony-forming activity. Furthermore, Xiang et al. have recently reported that GPC3 is also not expressed in human mammary cancer (Xiang Y. Y. et al., Oncogene 20, 7408-7412 (2001)). These data suggest that GPC3 can act as a negative regulator in growth of these types of cancer. Specifically, GPC3 expression is reduced during tumor advancement in a type of cancer arising from adult GPC3-positive tissue. Furthermore, such reduction may play some roles in the development of a malignant phenotype.

In contrast, in the case of HCC, a tumor arises from a liver tissue wherein GPC3 is expressed only in fetal stage. Moreover, GPC3 expression tends to appear again at the time of transformation to malignancy. It is unclear whether or not such re-expression of GPC3 is important for advancement of such tumor. For the last few years, it has been revealed that cell surface heparan sulfate proteoglycan (HSPG) is required for the optimal activity of a heparin-binding growth factor such as a fibroblast growth factor (FGF) or Wnt (Yayon A. et al., Cell 64, 841-848 (1991); and Schlessinger J. et al., Cell 83, 357-360 (1995)). Glypicans constitute a GPI-anchored cell surface HSPG family. It is thus inferred that tissue-specific differences in the relation between tumorigenesis and GPC3 expression level are due to the fact that GPC3 regulates growth and survival factors differently in each tissue. GPC3 probably functions as a carcinoembryonic protein at least in these organs. It is not generally thought that a carcinoembryonic protein plays an important role in tumor advancement. However, the carcinoembryonic protein has been used as a tumor marker or a target of immunotherapy (Coggin J. H. Jr., CRC Critical Reviews in Oncology/Hematology 5, 37-55 (1992); and Matsuura H. and Hakomori S.-I., Proc. Natl. Acad. Sci. USA 82, 6517-6521 (1985)). Whether or not the carcinoembryonic behavior of GPC3 can be used for clinical applications and whether or not the re-expression of such glypican is important for HCC advancement remain to be studied.

DISCLOSURE OF THE INVENTION

Examples of tumor markers for melanoma include serum LDH, 5-S-cysteinyldopa (5-S-CD) that is broadly used in Japan, and an S-100β protein and a melanoma inhibitory activity (MIA) that have been reported as more sensitive markers in recent years. However, none of these tumor markers yield positive results unless the melanoma tested for is at a highly advanced stage, such as Stage IV. Therefore, it must be said that the usefulness of these tumor markers is limited in terms of early diagnosis of and early detection of postoperative recurrence of melanoma. Early diagnosis of melanoma requires another useful tumor marker. Specifically, an object to be achieved by the present invention is to provide a novel and clinically useful diagnostic agent for malignant melanoma.

The present inventors have previously identified glypican 3 (GPC3) as a novel carcinoembryonic protein that is overexpressed specifically in human hepatocellular carcinoma based on cDNA microarray analysis. Furthermore, the present inventors have detected a soluble GPC3 protein in the sera of HCC patients, thus revealing that GPC3 can be a novel tumor marker for HCC. At this time, the present inventors have discovered for the first time that GPC3 is expressed in a mouse melanoma cell line B16. The present inventors have considered that GPC3 is highly expressed also in melanoma in a manner similar to that in HCC and that GPC3 can be a useful tumor marker. As a result of experiments for confirmation, the present inventors have revealed that GPC3 is a non-conventional tumor marker for melanoma, with which early diagnosis can be performed. The present invention has been completed based on these findings.

The present invention provides the following (1) to (6):

(1) A diagnostic agent for malignant melanoma, which comprises an antibody against GPC3, or a probe or a primer capable of detecting GPC3 expression;
(2) A kit for diagnosing malignant melanoma, which comprises an antibody against GPC3, or a probe or a primer capable of detecting GPC3 expression;
(3) A diagnostic method for malignant melanoma, which comprises detecting or measuring GPC3 in a sample;
(4) The diagnostic method according to (3), which comprises causing a sample to come into contact with an antibody against GPC3;
(5) The diagnostic method according to (3) or (4), which comprises quantifying GPC3 in a sample; and
(6) A method of using GPC as a tumor marker for malignant melanoma.

A: GPC3 mRNA Expression in Mouse Cell Lines

Lane 1: EL4, Lane 2: Colon26, Lane 3: B16, Lane 4: MH129F, Lane 5: MH129P, and Lane 6: MH134

As a result, the B16 melanoma cell line showed strong expression of GPC3 mRNA. However, EL4, Colon26, MH129F, MH129P, and MH134 showed no such expression.

B: GPC3 mRNA Expression in Human Melanoma Cell Line

Lane 1: 164, Lane 2: 888mel, Lane 3: Ihara, Lane 4: CRL1579, Lane 5: 526mel, Lane 6: G361, Lane 7: MeWo, Lane 8: SK-MEL-28, Lane 9: SK-MEL-19, Lane 10: Colo38, Lane 11: HMV-I, and Lane 12: HEMn (melanocyte)

Figure 1:
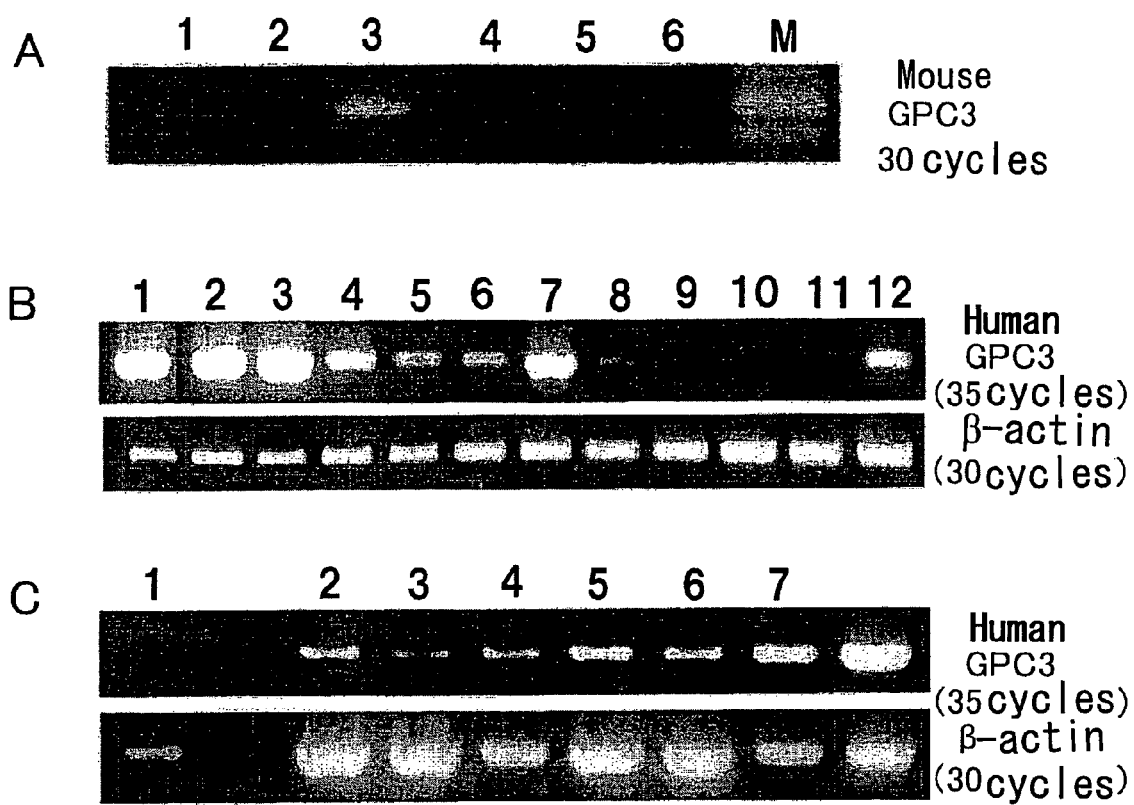
FIG. 1 shows GPC3 mRNA expression.

The 164, 888mel, Ihara, CRL1579, and MeWo melanoma cell lines showed strong expression of GPC3 mRNA. The 526mel, G361, and SK-MEL-28 cell lines showed moderate expression of GPC3 mRNA. However, SK-MEL-19, Colo38, and HMV-I showed no such expression (FIG. 1B). In addition, cultured melanocytes somewhat showed GPC3 mRNA expression to some extent.

C: GPC3 mRNA Expression in Human Melanoma Tissue

Lane 1: normal skin, Lane 2: Pt1 melanoma initial lesion, Lane 3: Pt2 melanoma initial lesion, Lane 4: Pt2 melanoma lymph node metastasis, Lane 5: Pt3 melanoma initial lesion, Lane 6: Pt4 melanoma initial lesion, Lane 7: congenital pigmented nevus case 1, and Lane 8: congenital pigmented nevus case 2

Normal skin showed no GPC3 mRNA expression, but most melanoma tissues showed GPC3 mRNA expression. On the other hand, congenital pigmented nevus also showed GPC3 mRNA expression.

Figure 2:
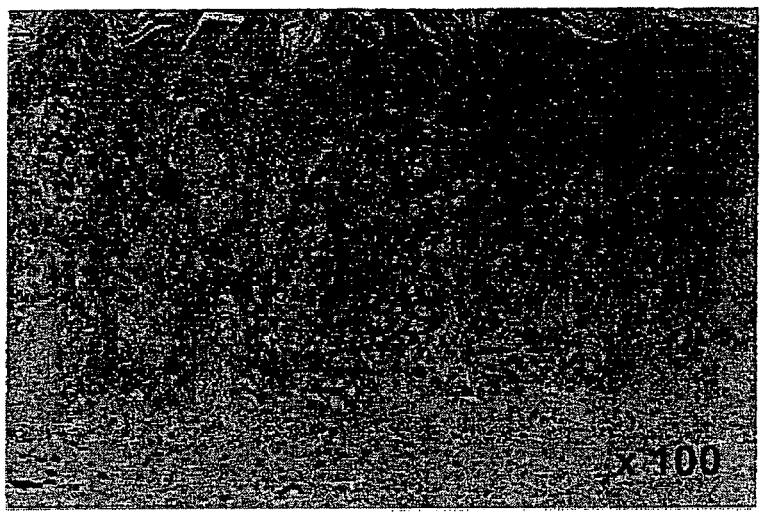
Figure 2:
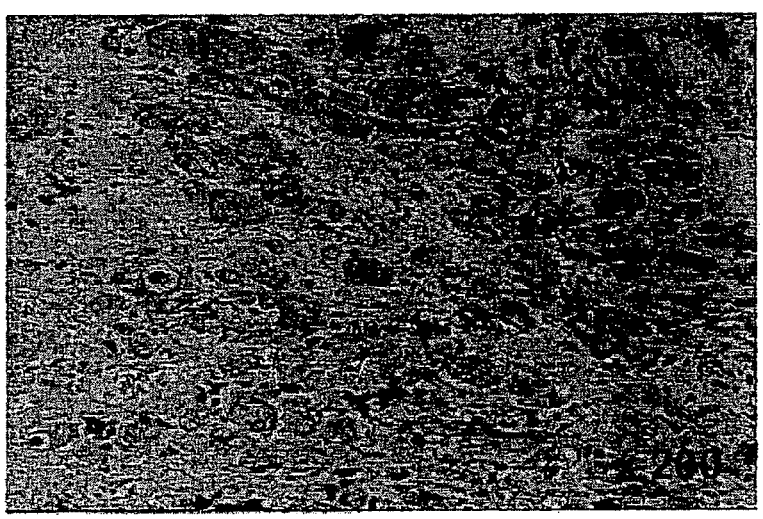
Figure 2:

FIG. 2 shows the GPC3 protein expression in melanoma and pigmented nevus as demonstrated by immunohistochemical analysis.

A: (Pt6) X100 Boundary Portion between GPC3 Melanoma (Cancerous) Portion and Non-Cancerous Portion, B: (Pt7) X200 GPC3 Melanoma (Cancerous) Portion, C: Pigmented Nevus Case 3 X100 GPC3

Whereas normal skin showed almost no GPC3 protein expression, melanoma cells and the pigmented nevus showed high expression of the GPC3 protein.

Figure 3:
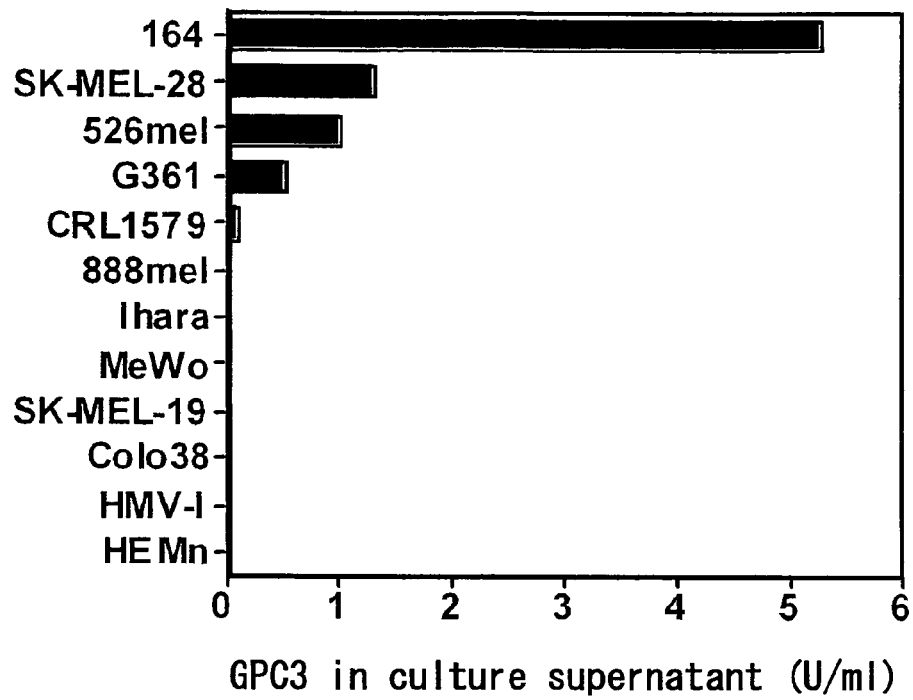
Figure 3:
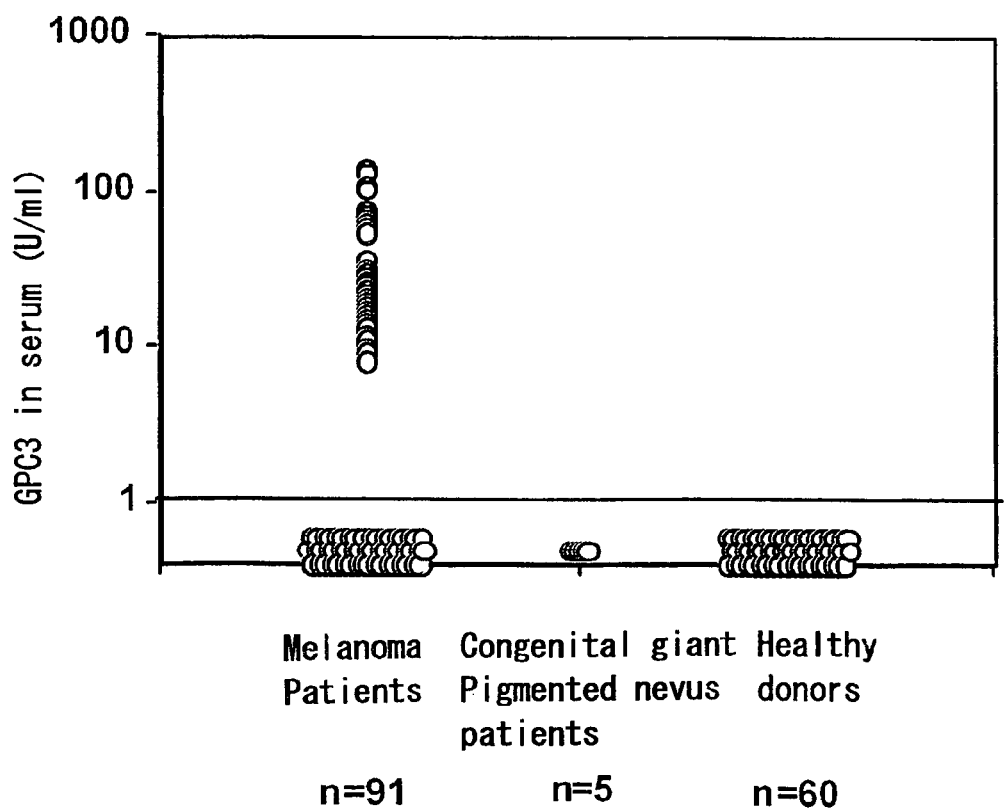

FIG. 3A shows the results of quantifying by ELISA the GPC3 protein secreted in culture supernatants of melanoma cell lines. The concentration of the GPC3 protein in 1 ml of each culture supernatant after 24 hours of culture of $1 \times 10^5$ HepG2 cells was defined as 1 U/ml. The GPC3 protein was detected in the culture supernatants of 5 out of 11 types of melanoma cell lines, although all such detected amounts were lower than that in the HepG2 culture supernatant.

FIG. 3B shows the presence of the soluble GPC3 protein in the sera of melanoma patients. GPC3 protein amounts in the sera of 91 preoperative melanoma patients, 5 congenital giant pigmented nevus patients, or 60 healthy donors (HDs) were evaluated by ELISA (FIG. 3B). No GPC3 proteins were detected in the sera of 60 HDs or in sera of 5 congenital giant pigmented nevus patients. 39.6% (36/91) of 91 melanoma patients, 0% (0/5) of 5 congenital giant pigmented nevus patients, and 0% (0/60) of HDs were positive for the GPC3 protein. Of these, in the sera of all 14 cases for which postoperative follow-up had been successfully performed, the GPC3 protein became undetected in the sera after excision operation.

Figure 4:
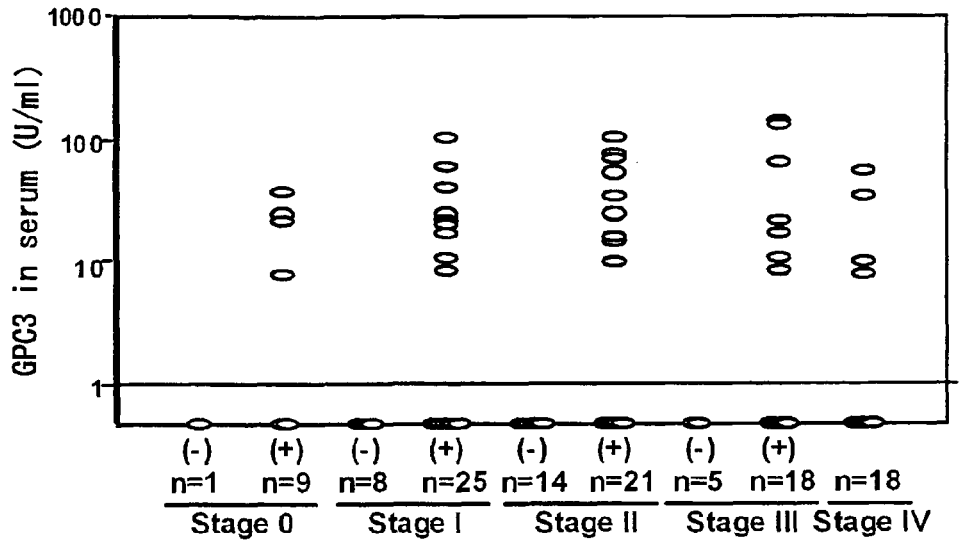
Figure 4:
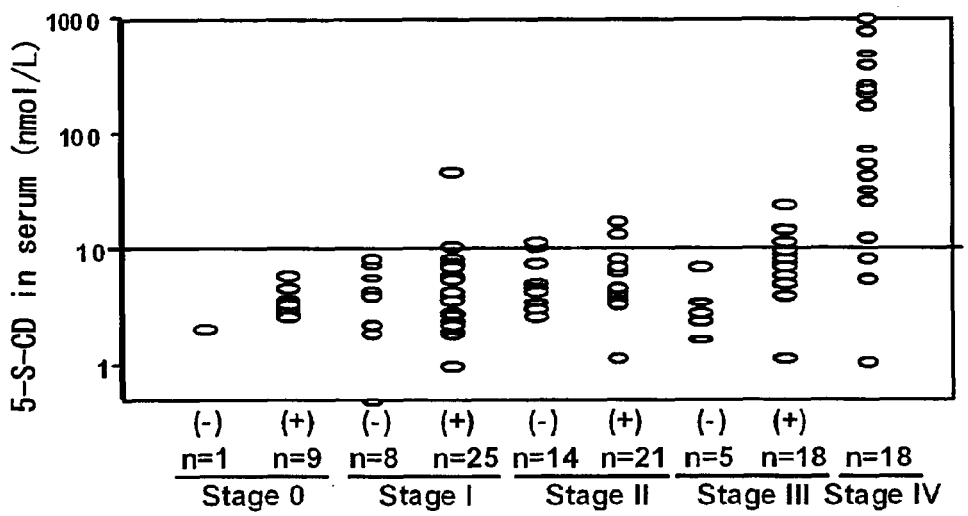
Figure 4:
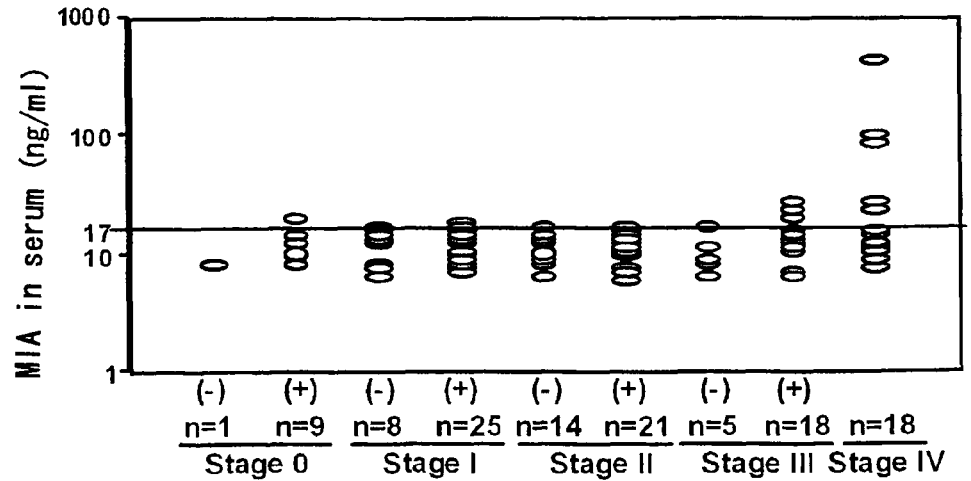

FIG. 4A shows the presence of the soluble GPC3 protein in the sera of melanoma patients at different stages. (+) denotes preoperative patients and (−) denotes cases where melanomas may be absent in postoperative patients. "N" denotes the number of cases.

FIG. 4B shows 5-S-CD in the sera of melanoma patients at different stages. 5-S-CD (nmol/L) values in FIG. 4B are of the same cases as those shown in FIG. 4A. The cutoff value was determined to be 10 (nmol/L).

FIG. 4C shows MIA in the sera of melanoma patients at different stages. MIA (ng/ml) values in FIG. 4C are those of the same cases as shown in FIG. 4A. The cutoff value was determined to be 17 (ng/ml).

BEST MODE FOR CARRYING OUT THE INVENTION

The present inventors have discovered that glypican 3 (GPC3) is a serum tumor marker that is useful for early diagnosis of melanoma with the use of the method described in (Nakatsura T. et al., Biochem. Biophys. Res. Commun. 306, 16-25 (2003)).

The amino acid sequence of the human GPC3 protein is known. The amino acid sequence has been deposited with the GenBank protein database under accession No. NP 004475 and is easily obtained by persons skilled in the art.

The present invention provides a diagnostic agent for malignant melanoma, which comprises antibody against GPC3, or a probe or a primer capable of detecting GPC3 expression.

The antibody against GPC3 can be prepared by a method known by persons skilled in the art (e.g., see "New Biochemical Experiment 1 (*Shin-Seikagaku Jikken Kouza* 1)," Protein I, pp. 389-406, TOKYO KAGAKU DOZIN CO., LTD.). The amino acid sequence of the GPC protein is known as described above. The GPC protein can be produced based on the amino acid sequence using general protein expression techniques. Alternatively, a commercially available GPC protein (Santa Cruz, Calif.) can also be used. Such commercially available GPC3 is preferably used after the removal of SDS with the use of SDS-Out™ (Sodium Dodecyl Sulfate Precipitation Reagent; purchased from PIERCE, Rockford, Ill.), if necessary. Moreover, a partial peptide of GPC3 can be produced by selecting an appropriate partial sequence from the amino acid sequence of GPC3 and then using general peptide synthesis techniques.

To prepare a polyclonal antibody, an appropriate amount of the GPC3 protein or a partial peptide thereof is administered to an animal such as a rabbit, a guinea pig, a mouse, or a fowl. The GPC3 protein may be administered together with an adjuvant (FIA or FCA) that promotes antibody production. Administration is generally performed every several weeks. Through a plurality of instances of immunization, the resulting antibody titer can be elevated. After final immunization, an anti-serum can be obtained by collecting blood from an immunized animal. The thus obtained anti-serum is subjected to fractionation by ammonium sulfate precipitation or anion chromatography, or affinity purification using protein A or an immobilized antigen, for example. Hence, a polyclonal antibody can be prepared. In the meantime, a monoclonal antibody can be prepared as follows. For example, an animal is immunized with the GPC3 protein or a partial peptide thereof in a manner similar to that of the above description. After final immunization, the spleen or the lymph node is collected from the immunized animal. Antibody-producing cells contained in the spleen or the lymph node are fused to myeloma cells using polyethylene glycol or the like, thereby preparing hybridomas. A hybridoma of interest is screened for and then the hybridoma is cultured. The monoclonal antibody can be prepared from the culture supernatant. Such monoclonal antibody can be purified through fractionation by ammonium sulfate precipitation or anion chromatography, or through affinity purification using protein A or an immobilized antigen, for example. In addition, an antibody that is used for the purpose of the present invention may be an antibody that recognizes any epitope of GPC3.

As an antibody that is used in the present invention, an immunoglobulin fraction prepared as described above may be used. Moreover, fractions such as $F(ab')_2$, Fab', and Fab obtained by separating only a site for binding with the GPC3 protein, can also be used.

In view of the accuracy of a diagnostic agent, an antibody that is used in the present invention is preferably a human type antibody or a human antibody. A mouse-human chimeric antibody that is an example of such human type antibody can be prepared by isolating an antibody gene from a mouse cell that produces an antibody against the GPC3 protein, recombining the H chain constant region with a human IgE H chain constant region gene, and then introducing the resultant into a mouse myeloma cell. Furthermore, a human antibody can be prepared by immunizing a mouse (in which the immune system has been replaced by a human immune system) with the GPC3 protein.

The antibody concentration in the diagnostic agent of the present invention is not particularly limited. For example, an antibody can be used at concentrations ranging from 0.1 μg/ml to 10 μg/ml. The diagnostic agent may appropriately contain a pharmaceutically acceptable carrier and the like, if necessary, in addition to the above antibody against GPC3.

The present invention further provides a diagnostic method for melanoma, which comprises detecting or measuring GPC3 in a sample. For example, GPC3 in a sample can be detected or measured by causing the sample to come into contact with an antibody against GPC3. Examples of a sample in the present invention include body fluids (e.g., sera, saliva, and urine) or skin tissue sections obtained from subjects who may be affected with melanoma. A particularly preferable sample is a serum, for example. A sample may be caused to come into contact with the above antibody based on a method that is generally performed in the art, and the method therefor is not particularly limited.

When a skin tissue section is used as a sample, a tissue section of an organ, which has been prepared according to a standard method, is subjected to immunostaining using an antibody against GPC3. The presence or the absence of GPC3 expression is observed through immunostaining, so that the presence or the absence of the development of malignant melanoma (melanoma) can be determined.

Moreover, when a body fluid such as a serum is used as a sample, the presence or the absence of the development of malignant melanoma can be determined by causing the sample to come into contact with the above antibody and then quantitatively detecting the specific binding between GPC3 (that can be present in the sample) and the antibody with the use of a fluorescent substance, a light-emitting substance, a secondary antibody, or the like, labeled with an enzyme or the like.

Specifically, in order to detect or measure GPC3 in a sample according to the method of the present invention, a sample is caused to react with an antibody against GPC3 and then a complex that is the reaction product is detected. Detection of a complex that is a reaction product is made possible by previously binding a label (e.g., an enzyme, a radioactive substance, or a fluorescent substance) to an antibody. Specifically, with the use of an antibody against GPC3, GPC3 is detected or measured by a known measurement method such as a sandwich method, a competitive method, an agglutination method, or a Western blotting method. Thus, malignant melanoma can be diagnosed.

Reaction for diagnosis may also be performed in the liquid phase such as in wells, or on solid-phase supports on which an antibody against GPC3 has been immobilized. In this case, through comparison with a standard value that has been previously determined using normal samples not affected with melanoma or samples known to be affected with melanoma, whether or not a measured value is melanoma-positive can be determined. Moreover, upon diagnosis, it is preferable to determine a cut-off value through measurement of serum GPC3 amounts in many melanoma patients and healthy subjects.

The diagnostic method of the present invention can be used for diagnosing whether or not a subject is affected with melanoma. Furthermore, the diagnostic method can also be performed over time so as to confirm therapeutic effects against melanoma.

Furthermore, when GPC3 is detected or measured in diagnosis of malignant melanoma according to the present invention, a method for detecting GPC3 mRNA may also be used in addition to the detection of GPC3 as a protein. Specifically, DNA or RNA capable of hybridizing to GPC3 mRNA is caused to react with a sample and then hybridization products of GPC3 mRNA in sample and DNA or RNA are detected. Examples of a method for detecting mRNA include an in situ hybridization method, a Northern blotting method, and an RT-PCR method. Specifically, according to the present invention, a diagnostic agent for malignant melanoma is provided, which comprises a probe or a primer capable of detecting GPC3 expression. The above probe or primer can be appropriately designed and obtained by persons skilled in the art based on the amino acid sequence (e.g., GenBank Protein Database, Accession No. NP 004475) of the known human GPC3 protein.

The present invention further provides a kit for diagnosing malignant melanoma, which comprises an antibody against GPC3 or a probe or a primer capable of detecting GPC3 expression. When the antibody against GPC3 is used, an example of the kit of the present invention is a kit that comprises a reagent required for analysis using a sandwich method, a competitive method, an agglutination method, a Western blotting method, or the like. Moreover, when the probe or primer capable of detecting GPC3 expression is used, an example of the kit of the present invention is a kit that comprises a reagent required for analysis using an in situ hybridization method, a Northern blotting method, an RT-PCR method, or the like.

Furthermore, the present invention also relates to a method of using GPC3 as a tumor marker for malignant melanoma. Examples of this method thus encompass all methods for diagnosing malignant melanoma by using GPC3 as a tumor marker for malignant melanoma. The embodiments of such method are not limited. Specific examples of such method that uses GPC3 as a tumor marker for malignant melanoma encompass a method that comprises detecting or measuring GPC3 in a sample by a sandwich method, a competitive method, an agglutination method, a Western blotting method, or the like using an antibody against GPC3 and a method that comprises detecting or measuring GPC3 expression in a sample by an in situ hybridization method, a Northern blotting method, RT-PCR method, or the like using a probe or a primer capable of detecting GPC3 expression.

The present invention will be further described specifically by referring to examples. However, the present invention is not limited by these examples.

EXAMPLES

Example 1

GPC3 mRNA Expression in Mouse Cell Lines

GPC3 mRNA expression was examined by reverse transcriptase-PCR (RT-PCR). MH129F, MH129P, and MH134 mouse cell lines were obtained from the Cell Resource Center for Biomedical Research, Institute of Development, Aging and Cancer, Tohoku University. EL4, Colon26, and B16 were donated by Dr. M. Ogawa of Kumamoto University.

RT-PCR was performed according to a known method (e.g., Nakatsura T. et al., Biochem. Biophys. Res. Commun. 281, 936-944 (2001)). Mouse GPC3 gene-specific PCR primers capable of amplifying a 500-bp fragment were designed. RT-PCR reaction was performed using the primers, and it consisted of 5 minutes of initial denaturation at 94° C. followed by 30 amplification cycles at an annealing temperature of 58° C. The GPC3 PCR primer sequences used herein were sense: 5'-ACGGGATGGTGAAAGTGAAGA-3' (SEQ ID NO: 1) and antisense: 5'-GAAAGAGAAAAGAGG-GAAACA-3' (SEQ ID NO: 2).

The mouse cell lines were compared in terms of GPC3 mRNA expression. As a result, the B16 melanoma cell line showed strong expression of GPC3 mRNA, but the EL4, Colon26, MH129F, MH129P, and MH134 lines showed no such expression (FIG. 1A).

Example 2

GPC3 mRNA Expression in Human Melanoma Cell Lines

PC3 mRNA expression was examined by reverse transcriptase-PCR (RT-PCR). G361, CRL1579, SK-MEL-28, HMV-I, and HMV-II melanoma cell lines were obtained from the Cell Resource Center for Biomedical Research, Institute of Development, Aging and Cancer, Tohoku University. 526mel and 888mel were donated by Dr. Y. Kawakami of Keio University. Moreover, Ihara, MeWo, and colo38 were donated by Dr. T. Kageshita of Kumamoto University. Furthermore, cultured human epidermal melanocytes, HEMn, were purchased from KURABO (KURABO INDUSTRIES LTD.).

RT-PCR was performed according to a known method (e.g., Nakatsura T. et al., Biochem. Biophys. Res. Commun. 281, 936-944 (2001)). Human GPC3 gene-specific PCR primers capable of amplifying a 939-bp fragment were designed. RT-PCR reaction was performed using the primers, and it consisted of 5 minutes of initial denaturation at 94° C. followed by 30 amplification cycles at an annealing temperature of 58° C. The GPC3 PCR primer sequences used herein were sense: 5'-GTTACTGCAATGTGGTCATGC-3' (SEQ ID NO: 3) and antisense: 5'-CTGGTGCCCAGCACATGT-3' (SEQ ID NO: 4). β-actin PCR primer sequences that were used for control experiments were sense: 5'-CCTCGC-CTTTGCCGATCC-3' (SEQ ID NO: 5) and antisense: 5'-GGATCTTCATGAGGTAGTCAGTC-3'(SEQ ID NO: 6).

After standardization with a control β-actin mRNA, melanoma cell lines were compared in terms of GPC3 mRNA expression. As a result, the 164, 888mel, Ihara, CRL1579, and MeWo melanoma cell lines showed strong expression of GPC3 mRNA. The 526mel, G361, and SK-MEL-28 cell lines showed moderate expression. However, the SK-MEL-19, Colo38, and HMV-I lines showed no such expression (FIG. 1B). In addition, cultured melanocytes showed expression to some extent.

Example 3

GPC3 mRNA Expression in Human Melanoma Tissues

Similarly, GPC3 mRNA expression in normal human skin, human melanoma, and human pigmented nevus tissues was examined. Specimens used herein were donated by Dr. T. Kageshita, for which informed consent had been obtained from donors treated at the Department of Dermatology, Kumamoto University School of Medicine. As a result, no GPC3 mRNA expression was observed in normal skin, but it was observed in most melanoma tissues. Furthermore, GPC3 mRNA expression was also observed in congenital pigmented nevus.

Example 4

GPC3 Protein Expression in Melanoma

Immunohistochemical analysis was performed on GPC3 in melanoma and non-cancerous regions in the periphery of melanoma tissues that had been excised from 21 melanoma patients, and in pigmented nevus and normal skin regions in the periphery of pigmented nevus tissues that had been excised from 11 pigmented nevus patients.

Immunohistochemical analysis was performed according to a method known in the art (Nakatsura T. et al., Biochem. Biophys. Res. Commun. 281, 936-944 (2001)). Each formalin-immobilized and paraffin-embedded tissue sample section with a thickness of 4 μm was stained together with an anti-GPC3 antibody that had been diluted at a ratio of 1:200. Typical results are shown in FIG. 2.

As shown in FIG. 2A and FIG. 2B, in the two melanoma cases, whereas almost no GPC3 protein was expressed in normal skin, the GPC3 protein was highly expressed in melanoma cells. On the other hand, as shown in FIG. 2C, the GPC3 protein was also highly expressed in pigmented nevus. The GPC3 protein was highly expressed in 17 out of 21 melanoma cases (81.0%) and in 10 out of 11 pigmented nevus cases.

Example 5

Presence of Soluble GPC3 Protein in the Culture Supernatants of Melanoma Cell Lines and in the Sera of Melanoma Patients For biotinylation of an anti-GPC3 rabbit polyclonal antibody (Santa Cruz, Calif.) that had been prepared against the recombinant protein corresponding to GPC3 303-464 amino acids, a FluoReporter Mini-Biotin-XX Protein Labeling Kit (F-6347) (Molecular Probes, Inc., Eugene) was used. A 96-well ELISA plate (Nunc, Denmark) was coated with 0.1 μg/well anti-human GPC3 303-464 (Santa Cruz) in PBS (pH 7.4) at 4° C. overnight. Subsequently, the plate was blocked using 100% Block Ace (Dainippon Pharmaceutical Co. Ltd.) at room temperature for 1 hour. A positive control standard sample, a culture supernatant, and the serum of a patient, which had been diluted 200-fold with 10% Block Ace, were added together with the biotinylated anti-GPC3 antibody, followed by 2 hours of incubation at room temperature. After 3 times of washing with PBS, HRP-Conjugated Streptavidin (ENDOGEN, Woburn) was added to each well. After 30 minutes of incubation, the plate was washed 3 times with PBS, and a TMB substrate solution (ENDOGEN) was added. An ELISA reader (model 550, Bio-Rad) was used at 405 nm for analysis.

After obtainment of informed consent, serum samples were obtained from melanoma patients treated at the Department of Dermatology, Kumamoto University School of Medicine. GPC3 is a GPI-anchored membrane protein. Furthermore, it has been reported that GPC3 may be a secretory protein (Filmus J., Glycobiology 11, 19R-23R (2001)). The present inventors previously reported that glypican-3 (GPC3) is a secretory protein, that the present inventors successfully detected glypican-3 (GPC3) in the sera of 40% of HCC patients with the use of the ELISA method, and that GPC3 is useful as a novel tumor marker for HCC (Nakatsura T. et al., Biochem. Biophys. Res. Commun. 306, 16-25 (2003)). Hence, the present inventors have attempted this time to detect the GPC3 protein so as to know whether or not the GPC3 protein is also secreted in melanoma.

Detection was performed by Enzyme-Linked Immunosorbent Assay (ELISA) using the anti-GPC3 303-464 antibody and the biotinylated anti-GPC3 antibody. With the use of a commercially available recombinant protein corresponding to GPC3 303-464, the accuracy of GPC3 quantification in the ELISA system was confirmed. A standard curve for quantification of the GPC3 protein was evaluated based on OD data using the serial dilution of a HepG2 culture supernatant. The concentration of the GPC3 protein in 1 ml of the culture supernatant after 24 hours of culture of $1\times10^5$ HepG2 cells was defined as 1 U/ml. The GPC3 protein was detected in the culture supernatants of 5 out of 11 types of melanoma cell lines, although all such detected amounts were lower than that of the GPC3 protein in the HepG2 culture supernatant. Furthermore, no GPC3 protein was detected in the culture supernatant of cultured melanocytes (FIG. 3A).

Next, the soluble GPC3 protein in the sera of melanoma patients was detected (FIG. 3B). Blood samples were collected from 91 preoperative melanoma patients. The patients' profiles were collected from medical records and then clinical stages were determined based on the TNM classification. The amounts of the GPC3 protein in the sera of 91 melanoma patients, 5 congenital giant pigmented nevus patients, and 60 healthy donors (HDs) were evaluated by ELISA (FIG. 3B). No GPC3 protein was detected in the sera of 60 HDs or in that of 5 congenital giant pigmented nevus patients. 39.6% (36/91) of 91 melanoma patients, 0% (0/5) of 5 congenital giant pigmented nevus patients, and 0% (0/60) of HDs were positive for the GPC3 protein. Of these cases, in all 14 cases for which postoperative follow-up had been successfully performed, the GPC3 protein became undetected in the sera after excision operation. Table 1 lists the presence of soluble GPC3, 5-S-CD, and MIA in the sera of the melanoma patients.

TABLE 1

| Stage | GPC3 | 5-S-CD | MIA |
|---|---|---|---|
| 0 | 4/9 (44.4%)[a] | 0/9 (0.0%) | 1/9 (11.1%) |
| I | 10/25 (40.0%) | 2/25 (8.0%) | 5/25 (20.0%) |
| II | 10/21 (47.6%) | 2/20 (10.0%) | 1/21 (4.8%) |
| III | 7/18 (38.9%) | 5/18 (27.8%) | 3/18 (16.7%) |
| IV | 5/18 (27.8%) | 15/18 (83.3%) | 9/18 (50.0%) |
| Total | 36/91 (39.6%) | 24/90 (26.7%) | 19/91 (20.9%) |

[a]Values significantly higher than the other values from the same clinical stage group are underlined.

As is clear from FIGS. 4A, B, and C and the results in Table 1, both a conventional tumor marker for melanoma, 5-S-CD (FIG. 4B), and a recently regarded tumor marker, MIA (FIG. 4C), are useful only for advanced melanomas at Stages III and IV. However, GPC3 (FIG. 4A) is effective for diagnosing melanomas even at early stages such as Stages 0, I, and II. Thus, it was revealed that GPC3 is useful as a novel tumor marker for melanoma. In addition, an MIA ELISA kit (Roche Germany) was used for measurement of MIA.

Table 2 shows the presence of soluble GPC3 in the sera of patients with melanomas classified based on visual classification.

TABLE 2

| Type | Percentage of GPC3 positive sera |
|---|---|
| ALM (acral lentiginous melanoma) | 15/44 (34.1%) |
| SSM (superficial spreading melanoma) | 9/16 (56.3%) |
| LMM/LM (lentigo maligna melanoma) | 4/9 (44.4%) |
| NM (nodular melanoma) | 2/5 (40.0%) |
| Mucous (mucous melanoma) | 3/12 (25.0%) |
| Total | 33/86 (38.4%) |

The results in Table 2 suggest that GPC3 has a somewhat greater advantage in terms of the diagnosis of superficial spreading melanoma or lentigo maligna melanoma, which is frequently found in Western people, rather than in terms of the diagnosis of acral lentiginous melanoma that occurs on the soles of feet, which is frequently found in Japanese people. It was concluded that GPC3 can sufficiently contribute to the diagnosis of melanomas not only in Japan, but also throughout the world.

INDUSTRIAL APPLICABILITY

According to the present invention, it was demonstrated that GPC3 is useful as a tumor marker with which melanoma at an early stage can be diagnosed. According to the present invention, the use of GPC3 as a tumor marker for melanoma enables the early and convenient diagnosis of whether or not a subject is affected with melanoma. GPC3 is very useful in applications pertaining to cancer diagnosis for many melanoma patients throughout the world.

The invention claimed is:

1. A method of determining an increased likelihood of the presence of malignant melanoma in a subject comprising:
   obtaining a sample from a subject at risk of having malignant melanoma;
   contacting the sample with an antibody against GPC3;
   quantitatively determining an amount of GPC3 detected in the sample;
   comparing the detected amount of GPC3 to a control value determined using samples from healthy subjects;
   concluding that an increased amount of GPC3 detected in the sample compared to the control value is indicative of an increased likelihood of the presence of malignant melanoma in the subject.

2. The method according to claim 1, wherein the sample comprises a body fluid or skin sample.

3. The method according to claim 2, wherein the sample is a body fluid comprising a serum sample.

4. The method according to claim 1, wherein the method comprises:
   detecting soluble or membrane-bound GPC3 protein using an antibody recognizing an extracellular domain of the protein along with additional clinically relevant melanoma tumor markers.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgggatggt gaaagtgaag a                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 2
gaaagagaaa agagggaaac a                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gttactgcaa tgtggtcatg c                                              21

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctggtgccca gcacatgt                                                  18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctcgccttt gccgatcc                                                  18

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggatcttcat gaggtagtca gtc                                            23